US006645407B2

(12) United States Patent
Kellenberger et al.

(10) Patent No.: US 6,645,407 B2
(45) Date of Patent: Nov. 11, 2003

(54) PROCESS FOR MAKING ABSORBENT MATERIAL WITH IN-SITU POLYMERIZED SUPERABSORBENT

(75) Inventors: Stanley R. Kellenberger, Appleton, WI (US); David Martin Jackson, Roswell, GA (US); Young C. Ko, Neenah, WI (US); Dave A. Soerens, Neenah, WI (US); Jason M. Laumer, Appleton, WI (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 105 days.

(21) Appl. No.: 10/017,684

(22) Filed: Dec. 14, 2001

(65) Prior Publication Data

US 2003/0111774 A1 Jun. 19, 2003

(51) Int. Cl.[7] .................. B29C 35/00; B29C 35/02; B29C 11/14
(52) U.S. Cl. ............... 264/115; 264/121; 264/122; 264/126
(58) Field of Search .................. 264/109–128

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,901,236 A | 8/1975 | Assarsson et al. |
| 4,076,663 A | 2/1978 | Masuda et al. |
| 4,100,324 A | 7/1978 | Anderson et al. |

(List continued on next page.)

FOREIGN PATENT DOCUMENTS

| | | | |
|---|---|---|---|
| DE | 199 05 947 A1 | 8/2000 | ............ A61L/15/60 |
| EP | 0 301 804 A2 | 2/1989 | ............ D04H/1/00 |
| EP | 0 301 804 A3 | 5/1990 | ............ D04H/1/56 |
| EP | 0 390 513 A2 | 10/1990 | ............ A61L/15/00 |
| EP | 0390 513 A3 | 8/1991 | ............ A61L/15/00 |
| EP | 0 402 650 A3 | 11/1991 | ............ A61L/15/22 |
| EP | 719 531 | 7/1996 | |
| EP | 729 336 | 6/1998 | |
| EP | 0 402 650 A2 | 12/1999 | ............ A61L/15/22 |
| WO | WO 95/13778 | 5/1995 | |
| WO | WO 98/51251 | 11/1998 | |
| WO | WO 99/34041 | 7/1999 | ............ D01F/6/36 |
| WO | WO 00/55418 | 9/2000 | |
| WO | WO 01/23177 | 4/2001 | |
| WO | WO 01/56625 A3 | 8/2001 | ............ A61L/15/00 |
| WO | WO 01/56625 A2 | 8/2001 | ............ A61L/15/00 |

OTHER PUBLICATIONS

English Translation of Abstract and Claims 1–10 of JP 11–93073A, Kao Corporation (2 pages).

*Primary Examiner*—Stephen J. Lechert, Jr.
(74) *Attorney, Agent, or Firm*—Pauley Petersen & Erickson

(57) ABSTRACT

A process for making an absorbent composite including absorbent fibers, superabsorbent polymer and, optionally, thermoplastic fibers and other ingredients is provided. The synthesis (i.e., polymerization) of the superabsorbent is completely integrated into the process for forming the absorbent composite. Specifically, the polymerization of superabsorbent is initiated from within a plurality of absorbent and/or thermoplastic fibers, which are then formed into a web. The integrated process eliminates the need for separate manufacture of superabsorbent polymer prior to the fiber forming and web forming processes. Also, the superabsorbent polymer thus formed tends to disperse better and remain adhered to the absorbent and/or thermoplastic fibers, providing a stable and uniform absorbent composite for various end use applications.

26 Claims, 3 Drawing Sheets

U.S. PATENT DOCUMENTS

| | | |
|---|---|---|
| 4,151,130 A | 4/1979 | Adams ................ 260/17.4 GC |
| 4,286,082 A | 8/1981 | Tsubakimoto et al. |
| 4,340,563 A | 7/1982 | Appel et al. |
| 4,443,492 A * | 4/1984 | Roller ........................ 427/501 |
| 4,500,315 A | 2/1985 | Pieniak et al. |
| 4,537,590 A | 8/1985 | Pieniak et al. |
| 4,540,454 A | 9/1985 | Pieniak et al. |
| 4,559,050 A | 12/1985 | Iskra |
| 4,560,372 A | 12/1985 | Pieniak |
| 4,596,567 A | 6/1986 | Iskra |
| 4,605,402 A | 8/1986 | Iskra |
| 4,676,784 A | 6/1987 | Erdman et al. |
| 4,818,464 A | 4/1989 | Lau |
| 4,888,238 A | 12/1989 | Katz et al. .................. 428/378 |
| 4,902,559 A | 2/1990 | Eschwey et al. |
| 5,059,664 A | 10/1991 | Yada et al. ................. 526/240 |
| 5,300,565 A | 4/1994 | Berg et al. ................. 525/54.2 |
| 5,350,624 A | 9/1994 | Georger et al. |
| 5,489,469 A | 2/1996 | Kobayashi et al. ......... 428/283 |
| 5,549,928 A | 8/1996 | Trokhan et al. |
| 5,674,478 A | 10/1997 | Dodd et al. |
| 5,821,179 A | 10/1998 | Masaki et al. |
| 5,962,068 A | 10/1999 | Tsuchiya et al. |
| 6,022,610 A | 2/2000 | Phan et al. |
| 6,086,950 A | 7/2000 | Masaki et al. |
| 6,261,679 B1 * | 7/2001 | Chen et al. .............. 428/317.9 |

* cited by examiner

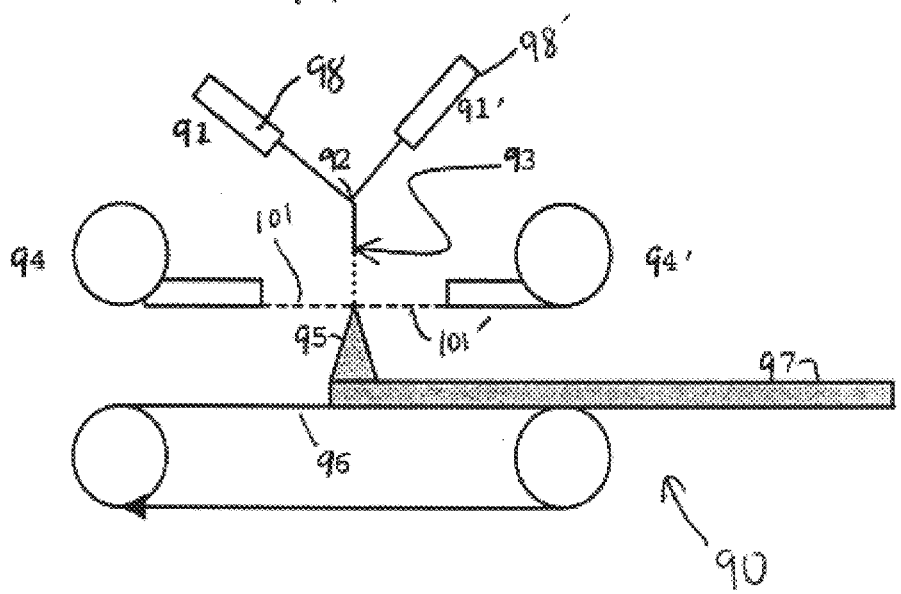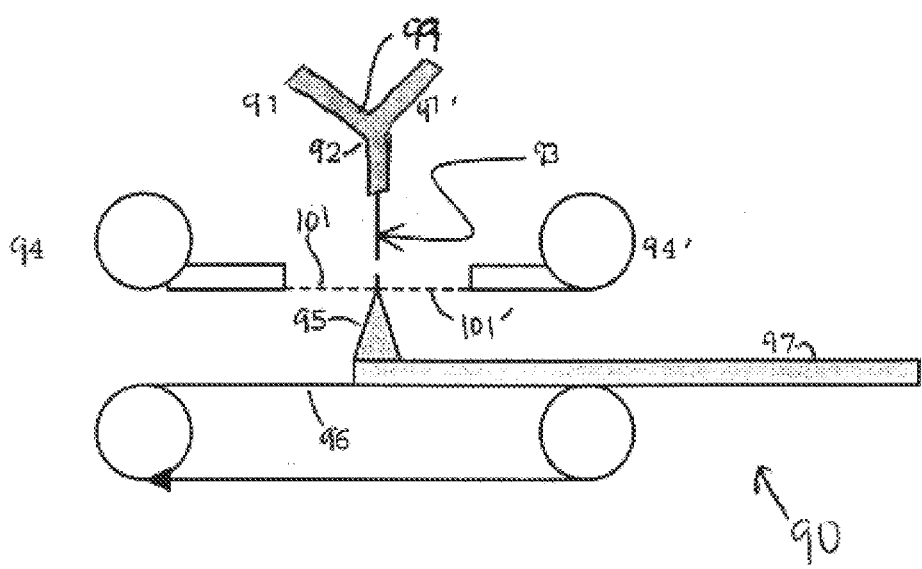

PROCESS FOR MAKING ABSORBENT MATERIAL WITH IN-SITU POLYMERIZED SUPERABSORBENT

FIELD OF THE INVENTION

This invention relates to a process for making absorbent material useful in personal care absorbent articles, medical absorbent articles and the like, in which a superabsorbent polymer component of the absorbent material is synthesized during manufacture of the absorbent material.

BACKGROUND OF THE INVENTION

Processes for forming absorbent composite materials from cellulose fibers and the like are known. U.S. Pat. No. 5,350,624 to Georger et al.; U.S. Pat. No. 4,902,559 to Eschwey et al.; U.S. Pat. No. 4,818,464 to Lau and U.S. Pat. No. 4,100,324 to Anderson et al. disclose processes for combining absorbent cellulose fibers with thermoplastic fibers to make absorbent composites. At least one meltblown die head, used for making meltblown fibers, is arranged near a chute, or as in the case of Eschwey the continuous fibers are spun into a duct containing fiberized pulp. Cellulose fibers and, possibly, other materials are injected from the chute into the nascent fiber stream while the fibers are forming. Pre-formed particles or fibers of superabsorbent material may also be added through the chute. These processes are generally referred to as "coform" processes.

Various processes for making superabsorbent polymers which are useful in absorbent composite materials are also known. U.S. Pat. No. 5,962,068, issued to Tsuchiya et al., discloses a process for producing a water-absorptive composite. First, an aqueous monomer solution containing a polymerizable monomer capable of producing a water-absorptive polymer is provided. Then, polymerization is initiated using a redox polymerization initiator. The resultant reaction mixture, which is partially polymerized, is applied dropwise onto a fibrous substrate. The polymerization is completed on the substrate.

One feature that the known processes have in common is that they require at least some separate process steps for polymerizing or partially polymerizing the superabsorbent material before it can be added to the forming process for the absorbent composite. In other words, neither process totally integrates the superabsorbent polymer formation with the ultimate process for forming the absorbent composite.

Definitions

The term "cellulose fibers" refers to fibers from natural sources such as woody and non-woody plants, regenerated cellulose, and derivatives from these fibers by means of chemical, mechanical or thermal treatment, or any combination of these. Woody plants include, for example, deciduous and coniferous trees. Non-woody plants include, for instance, cotton, flax, esparto grass, milkweed, straw, jute hemp, and bagasse. Regenerated cellulose fibers include, for instance, viscose and rayon. The cellulose derivatives include, for instance, microcrystalline cellulose, chemically crosslinked fibers, and chemically uncrosslinked, twisted fibers.

The term "average pulp fiber length" refers to a weighted average length of pulp determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_1>0}^{k} (X_1 * n_i)/n$$

where
k=maximum fiber length,
$X_i$=individual fiber length,
$n_i$=number of fibers having length $X_i$
and n=total number of fibers measured.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns. In both cases above the fibers are attenuated to their final diameter by aerodynamic drawing processes.

The term "staple filaments or fibers" means filaments or fibers which are natural or which are cut from a manufactured filament prior to forming into a web, and which have a length ranging from about 0.1 –15 cm, more commonly about 0.2–7 cm.

The term "microfibers" means small diameter fibers having an average diameter not greater than about 75 microns, for example, having an average diameter of from about 0.05 micron to about 50 microns, or more particularly, having an average diameter of from about 0.1 micron to about 10 microns, or even more typically 0.5 micron to about 5 microns.

The term "substantially continuous filaments or fibers" refers to filaments or fibers prepared by extrusion from a spinnerette, including without limitation spunbonded and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "nonwoven fabric or web" means a web having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, melt-blowing processes, spunbonding processes, air laying processes, and bonded carded web processes. The term also includes films that have been perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "wettable" and/or "hydrophilic" is meant to refer to a fiber which exhibits a liquid such as water, synthetic urine, or a 0.9 weight percent aqueous saline solution, in air contact angle of less than 90°. The contact angle may be determined, for example, in accordance with ASTM D724-89.

The term "thermoplastic" is meant to describe a material that softens and flows when exposed to heat and which substantially returns to its original hardened condition when cooled to room temperature.

The term "superabsorbent polymer precursor composition" refers to any and all solutions which, when mixed, chemically reacts to form a superabsorbent polymer. Each solution may be comprised of any combination of oligomer(s), monomer(s), crosslinking reagent(s), neutralizing agent, or initiator(s). In instances when only a single solution is utilized all the desired components must be in said solution and the initiator(s) must require a later activation step (e.g. heating or irradiation). In instances when two or more solutions are utilized the initiator(s) is most often, but not limited to, a chemical redox pair. When a redox pair, comprised of an oxidizing radical generator and a reducing agent, is used as the initiator the oxidizing radical generator and reducing agent must be in separate solutions. The solution of oxidizing radical generator or reducing agent may also contain any combination of oligomer(s), monomer(s), crosslinking reagent(s), or neutralizing agent.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of an elongating force, permits that material to be stretchable to a stretched length which is at least about 25 percent greater than its relaxed length, and that will cause the material to recover at least 40 percent of its elongation upon release of the stretching elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force.

The term "recover" or "retract" relates to a contraction of a stretched material upon termination of an elongating force following stretching of the material by application of the elongating force.

The term "superabsorbent material" refers to a water swellable, water-insoluble organic or inorganic material capable, under the most favorable conditions, of absorbing at least about 15 times its weight, preferably at least about 20 times its weight in an aqueous solution containing 0.9% by weight sodium chloride. The term "absorbent material" refers to any material capable of absorbing from about 5 to less than about 15 times its weight of the same solution.

The term "personal care absorbent article" includes diapers, training pants, swim wear, absorbent underpants, adult incontinence products, feminine hygiene products, and the like.

The term "medical absorbent article" includes medical absorbent garments, drapes, gowns, bandages, wound dressings, underpads, wipes, and the like.

The term "tissue and towel article" includes facial and bathroom tissues, paper towels, wet wipes, and the like.

SUMMARY OF THE INVENTION

The present invention is directed to a process for making an absorbent composite nonwoven web in which polymerization of superabsorbent is completely integrated into the process for forming the fibrous nonwoven web substrate. The process may include the step of forming a plurality of particles, fibers or fibrils from the reacting superabsorbent polymer mixture of precursor materials. The process will then further include the step of providing at least one primary gas stream to contain the polymerizing superabsorbent material and carry it away from the extrusion or combining apparatus. An additional gas stream may be provided to contain the thermoplastic fibers (if provided) and carry them away from the extrusion apparatus. This additional gas stream may also, contain and carry at least one superabsorbent polymer precursor composition while a similar gas stream may carry an ingredient to cause the superabsorbent polymer precursor composition to begin polymerizing. The process further includes the steps of providing at least one secondary gas stream carrying a plurality of hydrophillic (for example, cellulose) fibers, merging the primary and secondary streams together to form an integrated stream containing a mixture of ingredients from the primary and secondary streams, and directing the integrated stream onto a forming surface to form the composite material.

One or more streams of superabsorbent polymer precursor composition are added to the cellulose fibers, staple fibers and/or thermoplastic fibers, desirably before the fibers contact the forming surface. This can be accomplished by a) adding the one or more streams of superabsorbent polymer precursor to the primary stream (with or without thermoplastic fibers) before it combines with the secondary stream, b) adding the one or more streams of superabsorbent polymer precursor to the cellulose fibers in the secondary stream before it combines with the primary stream, c) adding a first stream of superabsorbent polymer precursor to the primary stream (with or without thermoplastic fibers), and adding a second stream of superabsorbent polymer precursor to the cellulose fibers in the secondary stream, before the two streams are combined, and/or d) adding one or more streams of superabsorbent polymer precursor to one or more tertiary gas streams which are combined into the integrated stream before the cellulose fibers (with or without thermoplastic fibers) contact the forming surface. Again, the thermoplastic fibers may be omitted and the primary stream may be used only to add the first stream of superabsorbent polymer precursor.

The one or more streams of superabsorbent polymer precursor may chemically react to form a superabsorbent polymer directly on the surfaces of the staple fibers, thermoplastic fibers and/or cellulose fibers, as the absorbent composite nonwoven web is being formed on the forming surface. Alternatively, the one or more streams of superabsorbent polymer precursor may partially or completely react to form a superabsorbent polymer before coming into contact with the forming surface. A further alternative is that the superabsorbent polymer precursor partially reacts so as to form particles, fibers or fibrils before coming into contact with other fibers (cellulose, staple, and/or thermoplastic) and finish polymerizing after in contact with these fibers and even after the nonwoven web is formed on the forming surface.

Other ingredients may also be added to the absorbent composite nonwoven web via the primary, secondary, tertiary and/or additional streams. These other ingredients may include, for instance, elastomeric fibers, less hydrophilic synthetic fibers (e.g., nylon and polyester), already formed superabsorbent particles or fibers, odor scavenging particles or fibers, bonding agents, wetting agents, and the like.

Additional surface crosslinking may also be performed on the absorbent material with in-situ polymerized superabsorbent once it is on the forming surface. Said surface crosslinking may enhance the absorbent properties of the material.

BRIEF DESCRIPTION OF THE DRAWINGS

FIG. 3 is a schematic view of a third embodiment of a coform apparatus useful in practicing the process of the invention; and FIG. 4 is a schematic view of a fourth embodiment of a coform apparatus useful in practicing the process of the invention.

DETAILED DESCRIPTION OF THE PRESENTLY PREFERRED EMBODIMENTS

Figure 1:
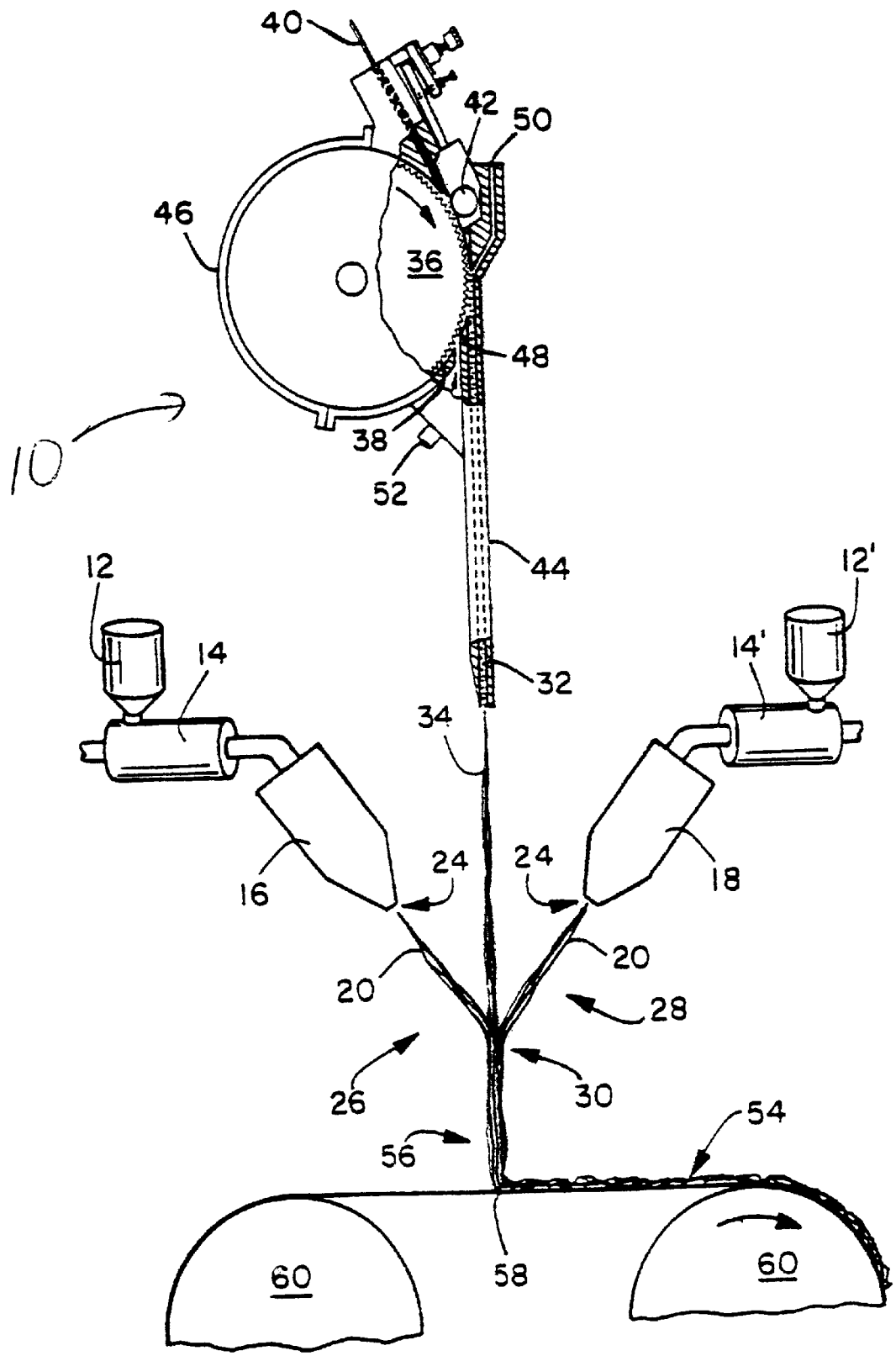
FIG. 1 is a schematic view of one embodiment of a coform apparatus useful in practicing the process of the invention.

FIG. 1 illustrates a coform apparatus as described in U.S. Pat. No. 5,350,624, issued to Georger et al., which is incorporated by reference. This apparatus can be used, with or without appropriate modification, to practice the process of the invention.

Referring to FIG. 1, apparatus 10 includes a pair of extruders 14, each associated with a hopper 12, feeding meltblowing dies 16 and 18 having die tips 24. Meltblowing dies 16 and 18 may be used to feed thermoplastic polymeric material into the first and second primary streams 20 as shown. Each meltblowing die is configured so that two streams of attenuating gas per die converge to form a single stream of gas which entrains and attenuates the molten threads in the primary streams 20, to form fibers or microfibers. Thus, each meltblowing die 16 and 18 has a corresponding single stream of gas 26 and 28 containing entrained and attenuated polymer fibers. The gas streams 26 and 28 containing polymer fibers are aligned to converge at an impingement zone 30.

A secondary stream 32, which may contain absorbent (e.g. cellulose) or other hydrophilic fibers (with or without particulates and other ingredients), are combined with the primary streams 20 containing the nascent fibers at the impingement zone 30. The combination of secondary streams 32 with the primary streams 20 of thermoplastic polymer fibers 24 is designed to produce a graduated distribution of absorbent fibers within the combined streams 20 of thermoplastic fibers. This may be accomplished by merging a secondary gas stream 34 containing the secondary stream of fibers 32, between the primary gas streams 26 and 28 containing the thermoplastic fibers, so that all three gas streams converge in a controlled manner into an integrated stream 56. The integrated stream 56 of combined fibers is deposited onto forming surface 58, resulting in formation of the absorbent composite material 54. The composite material 54 may be stored on one or more rolls 60.

The fiber forming apparatus for the secondary stream of fibers includes a conventional picker roll 36 arrangement which has a plurality of teeth 38 adapted to separate a matt or batt 40 of cellulose or other fibers into the secondary stream of individual fibers 32. The matt or batt of secondary fibers may include cellulose fibers, less hydrophilic staple fibers, or both. Desirably, the secondary fibers 32 are absorbent fibers. A housing 46 encloses the picker roll 36 and provides a passageway or gap 48 between the housing 46 and the surface of the teeth 38 of the picker roll 36. A gas such as air is supplied to the gap 46 by way of a gas duct 50. The gas duct 50 may enter the gap 46 at the junction 52 of the nozzle 44 and gap 48. The gas is supplied in sufficient quantity to convey the secondary fibers 32 through the nozzle 44, as well as aiding in removing secondary fibers 32 from teeth 38 of picker roll 36. Additives and/or other materials may be added to or entrained in the gas stream to treat the secondary fibers. The secondary stream of fibers 32 leaves the nozzle 44 at about the same velocity which the secondary fibers 32 leave the teeth 38 of picker roll 36.

In accordance with the invention, one or more superabsorbent polymer precursor compositions are added to the primary streams 20, the secondary stream 32, and/or the combined stream 56 before the combined stream 56 contacts the forming surface 58. For instance, a first polymer precursor composition may be added to one or both of the primary streams 20 and a second polymer precursor composition may be added to the secondary stream 32. Alternatively, only a single superabsorbent polymer precursor composition may be added to one or more of the primary and/or secondary streams 20 and 32, which precursor composition contains all of the reactive ingredients. Alternatively, the meltblown fibers can be completely eliminated from one or both primary streams 20, and one or both primary streams 20 may be used to convey only the above-mentioned first polymer precursor composition and second polymer precursor composition, or a single combined polymer precursor composition. Alternatively, the superabsorbent polymer precursor composition(s) can be added to the integrated stream 56 using one or more additional, i.e., tertiary streams (not shown). The apparatus of FIG. 1 may be modified in any appropriate fashion to facilitate the addition of the one or more superabsorbent polymer precursor compositions.

A wide variety of superabsorbent polymer precursor compositions may be employed in the process of the invention. At least one polymer composition may include a monomer. Suitable superabsorbent-forming monomers include the following monomers and combinations thereof:

1. Carboxyl group-containing monomers: monoethylenically unsaturated mono or poly-carboxylic acids, such as (meth)acrylic acid (meaning acrylic acid or methacrylic acid. Similar notations are used hereinafter), maleic acid, fumaric acid, crotonic acid, sorbic acid, itaconic acid, and cinnamic acid;
2. Carboxylic acid anhydride group-containing monomers: monoethylenically unsaturated polycarboxylic acid anhydrides (such as maleic anhydride);
3. Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate, sodium maleate, methylamine maleatel;
4. Sulfonic acid group-containing monomers: aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2-hydroxy-3-(meth) acryloxy propyl sulfonic acid];
5. Sulfonic acid salt group-containing monomers: alkali metal salts, ammonium salts, amine salts of sulfonic acid group containing monomers as mentioned above;
6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth)acrylate, triethylene glycol (meth)acrylate, poly(oxyethylene oxypropylene) glycol mono (meth)allyl ether (in which hydroxyl groups may be etherified or esterified);
7. Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth) acrylamide, N,N-dihydroxyalkyl (meth)acrylamides [such as N,N-dihydroxyethyl (meth)acrylamide, vinyl lactams (such as N-vinylpyrrolidone);
8. Amino group-containing monomers: amino group-containing esters (e.g., dialkylaminoalkyl esters, dihydroxyalkylaminoalkyl esters, morpholinoalkyl esters, etc.) of monoethylenically unsaturated mono-or di-carboxylic acid [such as dimethylaminoethyl (meth) acrylate, diethylaminoethyl (meth)acrylate, morpholinoethyl (meth)acrylate, dimethyl aminoethyl fumarate, heterocyclic vinyl compounds such as vinyl pyridines (e.g., 2-vinyl pyridine, 4-vinyl pyridine, N-vinyl pyridine), N-vinyl imidazole;
9. Quaternary ammonium salt group-containing monomers: N,N,N-trialkyl-N-(meth) acryloyloxyalkylammonium salts [such as N,N,N-trimethyl-N-(meth)acryloyloxyethylammonium chloride, N,N,N-triethyl-N-(meth) acryloyloxyethylamonnium chloride, 2-hydroxy-3-(meth)-acryloyloxypropyl trimethyl ammonium chloride]; and
10. Ether group-containing monomers: methoxy polyethylene glycol (meth)acrylate; polyethylene glycol dimethacylate.

Desirably, superabsorbent forming monomers suitable for the process of the invention include without limitation aliphatic unsaturated monocarboxylic acids or salts thereof; specifically unsaturated monocarboxylic acids or salts thereof such as acrylic acid or salts thereof, methacrylic acid or salts thereof, or unsaturated dicarboxylic acids or salts thereof such as maleic acid or salts thereof, itaconic acid or salts thereof, which may be used alone or in combination.

Among these, acrylic acid or salts thereof and methacrylic acid or salts thereof are preferred, with especially preferred being acrylic acid or salts thereof.

Polymerizable monomers giving a water-absorbing polymer in the present invention are preferably aliphatic unsaturated carboxylic acids or salts thereof as described above, therefore, aqueous solutions of these polymerizable monomers are preferably aqueous solutions essentially containing an aliphatic unsaturated carboxylic acid or a salt thereof. As used here, the expression "essentially containing an aliphatic unsaturated carboxylic acid or a salt thereof" means that the aliphatic unsaturated carboxylic acid or a salt thereof is contained at 50 mol % or more, preferably 80 mol % or more on the basis of the total amount of the polymerizable monomer.

Suitable salts of aliphatic unsaturated carboxylic acids normally include water-soluble salts such as alkali metal salts, alkali earth metal salts, ammonium salts or the like. The neutrality is appropriately selected depending on the purpose, but 20–90 mol % of carboxyl group is preferably neutralized with an alkali metal salt or an ammonium salt in the case of acrylic acid. If the partial neutrality of an acrylic monomer is less than 20 mol %, the resulting water-absorbing polymer tends to have low water-absorbing capacity.

Acrylic monomers can be neutralized with alkali metal hydroxides or bicarbonates or ammonium hydroxide or the like, preferably alkali metal hydroxides such as sodium hydroxide and potassium hydroxide.

Superabsorbent-forming monomers may also include comonomers which are polymerizable along with any of the monomers listed above. The comonomers may form part of the same superabsorbent polymer precursor composition as the primary monomer, or may be part of a different superabsorbent polymer precursor composition, and may be added to the fibrous mixture using the same or different streams. Where the primary monomer is an aliphatic unsaturated carboxylic acid, suitable comonomers include without limitation secondary monomers such as (meth) acrylamide, (poly)ethylene glycol (meth)acrylate, 2-hydroxyethyl (meth)acrylate or even slightly water-soluble monomers including acrylic-capped urethanes, acrylic alkyl esters such as methyl acrylate or ethyl acrylate may also be copolymerized in an amount within a range that does not affect performance of the resulting water-absorbing polymers in the present invention. As used herein, the term "(meth)acryl" means both "acryl" and "methacryl."

Aliphatic unsaturated carboxylic acids or salts thereof, especially acrylic acid or salts thereof sometimes form a self-crosslinked polymer by themselves, but may be positively induced to form a crosslinked structure using a crosslinker. The use of a crosslinker normally improves water-absorbing performance of the resulting water-absorbing polymer. Preferably, suitable crosslinkers include divinyl compounds copolymerizable with said polymerizable monomers such as N,N'-methylenebis(meth)acrylamide, (poly)ethylene glycol (meth)acrylate and water-soluble compounds having two or more functional groups capable of reacting with a carboxylic acid including polyglycidyl ethers such as ethylene glycol diglycidyl ether, polyethylene glycol diglycidyl ether. Among them, N,N'methylenebis(meth)acrylamide is especially preferred. Crosslinkers are used in an amount of 0.001–1% by weight, preferably 0.01–0.5% by weight on the basis of the amount of the monomer, and may be added in the same superabsorbent polymer precursor composition as the monomer, or as part of a different precursor composition.

The concentration of polymerizable monomers in an aqueous polymerizable monomer solution essentially containing an aliphatic unsaturated carboxylic acid or a salt thereof as described above is 20% or more, preferably 25% or more. Concentrations less than 20% by weight are not preferred because droplets having an appropriate viscosity are difficult to produce whereby the resulting water-absorbing polymer has insufficient water-absorbing capacity. The upper limit is preferably about 80% by weight in respect of handling of the polymerization reaction solution.

One or more polymerization initiators may be added in the same or a different superabsorbent polymer precursor composition as the monomer(s). The polymerization initiator may be added as part of the same precursor composition as the monomer if subsequent activation is required or if the initiator is a single component of a redox pair. Alternatively, the polymerization initiator may be added as part of a different precursor composition as the monomer due to the fact that the polymerization initiators may act quickly to polymerize the monomer units once contact is made.

Referring to FIG. 1, for instance, one precursor composition containing the oxidizing radical generator may be added using one of the primary streams 20 and a second precursor composition containing the reducing agent may be added using the other primary stream 20. Thus, each precursor composition may consist solely of the corresponding component of a redox pair or either/both precursor composition may additionally consist of any combination of oligomer(s), monomer(s), crosslinking reagent(s), neutralizing agent. In this regard, these superabsorbent polymer precursor compositions may be the sole component of one or both primary streams 20, or may be added along with meltblown fibers and/or other fiber types to either stream. When the two primary streams, along with the secondary stream 32 which may contain any combination of oligomer(s), monomer(s), crosslinking reagent(s), neutralizing agent, cellulose fibers and/or other optional ingredients, converge at the impingement zone 30, the polymerization reaction proceeds after the polymerization initiators are brought into contact with one another. In a similar manner, the above example may also include the instance when both primary streams 20 contain the same redox pair component (either the oxidizing radical generator or reducing agent) and secondary stream 32 contains the corresponding redox pair component.

Alternatively, also referring to FIG. 1, a first precursor composition containing the monomer(s) may be added using one or both primary streams 20. In this regard, the first superabsorbent polymer precursor composition may be the sole component of one or both primary streams 20, or may be added along with meltblown fibers or other fiber types to either stream. A second precursor composition containing the polymerization initiator(s) may be added alone or along with cellulose fibers and other optional ingredients to the secondary stream 32. When the primary and secondary streams converge at the impingement zone 30, the polymerization reaction proceeds after the polymerization initiator(s) are brought into contact with the monomer(s).

Polymerization initiators suitable for the present invention include without limitation somewhat water-soluble redox systems combining an oxidizing radical generator and a reducing agent. Such oxidizing agents include hydrogen peroxide, potassium bromate, N-bromosuccinimide, persulfates such as ammonium persulfate, sodium persulfate, or potassium persulfate, peroxides including hydroperoxides such as 1-butyl hydroperoxide or cumene hydroperoxide, secondary cerium salts, permanganates, chlorites, hypochlorites, etc., among which hydrogen peroxide is especially preferred. These oxidizing agents may be used in an amount of 0.001–10% by weight, desirably 0.01–2% by weight on the basis of polymerizable monomers.

Reducing agents are also used with the redox system, and may be added as part of the polymerization initiator. Suitable reducing agents are capable of forming a redox system with said oxidizing agents, specifically sulfites such as sodium sulfite or sodium hydrogensulfite, sodium thiosulfate, cobalt acetate, copper sulfate, ferrous sulfate, ferrous ammonium sulfate, sodium metabisulfite, tertiary amines or diamines, L-ascorbic acid or L-ascorbic acid alkali metal salts, etc. Among others, L-ascorbic acid or L-ascorbic acid alkali metal salts are especially preferred. These reducing agents are used in an amount of 0.001–10% by weight, preferably 0.01–2% by weight on the basis of polymerizable monomers. Desirably, the precursor composition containing the oxidizing radical generator is added using a different addition stream than is used for the reducing agents.

Process conditions should be tailored so as to produce the desired type of structure. Exemplary process conditions are disclosed, for instance, in Table 1 of the above-mentioned U.S. Pat. No. 5,350,624, which is incorporated by reference. The process conditions may be tailored to produce an absorbent nonwoven web composite having the following compositions:

| | Composition, % By Weight | | |
|---|---|---|---|
| | Absorbent Fibers | Superabsorbent Polymer Formed In Situ | Thermoplastic Meltblown and/or Staple Fibers |
| Broad | 1–90 | 10–99 | 0–85 |
| Intermediate | 20–85 | 15–80 | 0–45 |
| Narrow | 30–70 | 30–70 | 10–30 |

Where a redox system of polymerization initiator(s) as described above is employed, the chemical reaction proceeds spontaneously. However, depending on the mechanism of chemical reaction employed, it may be desirable to adjust the temperature of the streams 20 and 32, velocities, distance above the forming surface where the streams are employed, and other process conditions needed to facilitate or optimize the chemical reaction. If molten thermoplastic polymer is extruded into the primary streams 20, some of the temperatures will need to be high, and will be controllable only within a range which permits proper extrusion of the polymer.

When conventional meltblown fibers are added to the primary streams 20, they may be formed from thermoplastic polymers including, without limitation, polyolefins, polyamides, polyester, polyurethane, polyvinyl alcohol, polycaprolactone or the like. Suitable polyolefins include without limitation polyethylene, polypropylene, polybutylene, copolymers of ethylene with other alpha-olefins, copolymers of propylene with other alpha-olefins, copolymers of butylene with other alpha-olefins, and combinations thereof.

Absorbent fibers are desirably added to the secondary stream 32. Desirably, the absorbent fibers include cellulose fibers. Examples of cellulose fibers include without limitation reconstituted cellulose (rayon), cotton, wood pulp fibers, wood pulp fluff, curled pulp fibers, microcrystalline cellulose, microfibrillar cellulose, and the like. Other hydrophilic fibers may also be employed, as well as synthetic thermoplastic staple fibers and synthetic elastomeric staple fibers. Blends of cellulose and non-cellulose fibers may also be employed, in any desired fashion to reach the desired level of absorbance or other desirable attributes like elasticity. Pre-formed superabsorbent particles or fibers may also be added. However, one advantage of employing superabsorbent polymer which is formed in situ is that it tends to adhere more strongly to the cellulose and other fibers in the secondary stream 32, resulting in a uniform and stable distribution of superabsorbent in the absorbent composite material 54. Thus, for purposes of the invention, the absorbent composite 54 includes at least some superabsorbent polymer formed in situ, whether or not pre-formed superabsorbent particles or fibers are added.

Examples of superabsorbent material polymers which may be formed in-situ include without limitation the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Known processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Pre-formed particulate superabsorbents are generally available in particle sizes ranging from about 20 to about 1000 microns. Examples of suitable commercially available particulate superabsorbents include Hydrasorb® P7050, available from BASF Corporation located in Portsmouth, Va., DRYTECH® 2035 available from Dow Chemical Co. located in Midland, Mich., and FAVOR® SXM 880, available from Stockhausen, Inc. located in Greensborough, N.C. An example of a fibrous superabsorbent is OASIS® 101, available from Technical Absorbents, located in Grimsby, United Kingdom.

Figure 2:
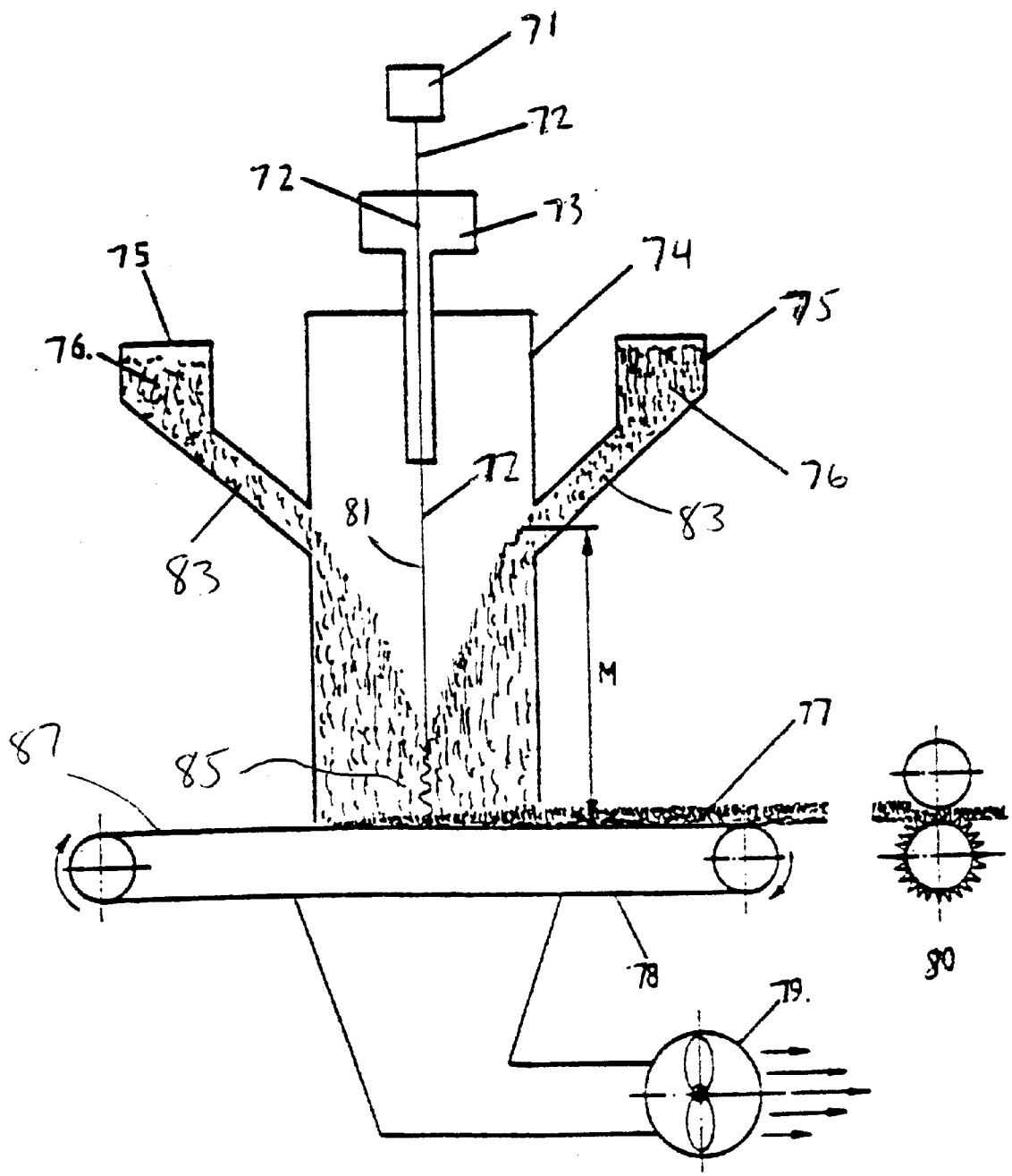
FIG. 2 is a schematic view of another embodiment of a coform apparatus useful in practicing the process of the invention.

FIG. 2 illustrates another example of a coform apparatus, which may be used, or modified for use in practicing the process of the invention. The coform apparatus of FIG. 2 is designed to form composite webs which contain continuous low air velocity drawn (i.e., spunbond) filaments instead of high air velocity drawn (i.e. meltblown) fibers. The apparatus of FIG. 2 is further described in U.S. Pat. No. 4,902,559 to Eschwey et al., which is incorporated by reference.

Referring to FIG. 2, one or more rows of continuous filaments 72 are spun through a long spinnerette 71 which has the same number of rows of orifices. The filaments 72, which represent the primary stream 81, pass through a guiding and stretching passage 73 where they are stretched to the desired extent by air blasts parallel to their direction of fall. The velocity of the air streams can be up to the velocity of sound. After passing through guiding passage 73, the continuous filaments 72 then pass into a shaft 74 the bottom third of which forms a mixing area M. In mixing area M the cellulose or other absorbent fibers 76, fed from a grinding mechanism 75, are fed into one or more secondary streams 83 and mixed with filaments 72 fed from the primary stream 81 to form a combined stream 85. Any preformed superabsorbent particles or other materials which may be added are also introduced in mixing area M. Air streams can also aid in the addition of fibers and particles, which enter on both sides of the rows of filaments.

The filaments and fibers, plus any additional materials, are deposited on a uniformly moving endless screen 78 and are held on the screen by a draft induced by an aspirating mechanism 79. The rate and manner of deposition of the filaments are controlled by the quantity of the filaments in the air and the aspirating conditions under the screen. Aspirating mechanism 79 should maintain a constant aspirating rate so that the current containing fibers and air is not reflected or horizontally deflected from the screen. The aspirated air can, after passing through a cleaning apparatus (not shown) be returned to the stretching area 73.

The sheet material 77 that forms then passes on for compression and consolidation in a heated embossing mechanism 80 having one smooth and one embossed roller.

In accordance with the invention, one or more superabsorbent polymer precursor compositions are added to the primary stream 81, the secondary stream 83, and/or the combined stream 85 before the combined stream 85 contacts the forming surface 87. For instance, a first polymer precursor composition may be added to the primary stream 81 and a secondary polymer precursor composition may be added to one or both secondary streams 83. Alternatively, only a single superabsorbent polymer precursor composition may be added to one or more of the primary and/or secondary steams 81 and 83, which precursor composition contains all of the reactive ingredients. Alternatively, the thermoplastic fibers may be eliminated from the primary stream 81, or the cellulose fibers may be completely eliminated from one of the secondary streams 83, and that stream can be used only to feed a superabsorbent polymer precursor composition. Alternatively, the superabsorbent polymer precursor composition(s) can be added to the integrated stream 85 using one or more additional, i.e., tertiary streams (not shown).

When using the apparatus of FIG. 2, the thermoplastic continuous filaments 72 may be formed from any of the thermoplastic polymers described above with respect to the meltblown fibers in FIG. 1. The cellulose fibers, and other materials injected into the secondary streams 83 may include any of the cellulose and other materials described with respect to FIG. 1. The superabsorbent polymer precursor composition may also include any of the monomers and other ingredients mixed above.

The superabsorbent polymer precursor composition(s) chemically react to form superabsorbent polymer in the primary stream 81 (if added there), the secondary stream(s) 83 (if added there), and/or the combined stream 85, and may continue reacting after the combined ingredients are deposited on the forming surface 87. Process conditions should be tailored so as to produce the desired type of structure. Exemplary process conditions are disclosed, for instance, in the above-mentioned U.S. Pat. No. 4,902,559, which is incorporated by reference. The process conditions may be tailored to produce an absorbent nonwoven web composite having the following compositions:

| | Composition, % By Weight | | |
|---|---|---|---|
| | Absorbent Fibers | Superabsorbent Polymer Formed In Situ | Thermoplastic Spunbond Fibers |
| Broad | 1–90 | 10–99 | 0–85 |
| Intermediate | 20–85 | 15–80 | 0–45 |
| Narrow | 30–70 | 30–70 | 10–30 |

FIGS. 3 and 4 illustrate two processes 90 in which two superabsorbent polymer precursor compositions are combined with each other and with other fibers before contacting the forming belt. Referring to FIGS. 3 and 4, nozzles 91 and 91' feed first and second superabsorbent polymer precursor compositions toward a junction 92 where they combine (and may begin reacting) in a combined precursor stream 93. Devices 94 and 94' may be fiberizers for forming hydrophilic fibers from bales (e.g. cellulose), and/or meltblown extruders for forming meltblown fibers, and for feeding the fibers into fiber streams 101 and 101'. The combined precursor stream 93 is combined with the fiber streams 101 and 101' to form a composite stream 95, which is then deposited onto a forming conveyor 96 as a pre-compacted absorbent composite material 97. The pre-compacted absorbent composite material 97 may then be compacted, bonded, or otherwise treated using conventional techniques to form an absorbent composite material of the invention.

The difference between FIGS. 3 and 4 is that, in the embodiment of FIG. 3, the nozzles 91 and 91' are part of two separate feed devices 98 and 98' which release the first and second superabsorbent polymer precursor compositions into separate streams which are then combined. In the embodiment of FIG. 4, the nozzles 91 and 91' are part of a single feed device 99 which combines the first and second superabsorbent polymer precursor compositions together before releasing the single combined precursor stream. In either case, the first and second superabsorbent polymer precursor compositions may begin reacting with each other upon contact, and in may continue reacting during the mixing and web forming stages, to form a superabsorbent polymer.

The resulting absorbent composite nonwoven material includes a plurality of hydrophilic fibers having superabsorbent particles formed in-situ which stick to the surfaces of the fibers, and which are not freely movable. Suitably, the superabsorbent particles are formed in-situ in such quantity which permits them to be spaced apart from each other by an average distance of about 50–4000 microns, desirably about 200–3000 microns, so that the superabsorbent particles may swell in the presence of liquid without contacting each other. Suitably, the in-situ formed superabsorbent particles have the same average diameter in the dry, unswollen state as conventional, pre-formed superabsorbent particles. The average dry particle diameter may range from about 10–1000 microns, desirably about 20–500 microns. A primary advantage of the absorbent composite materials of the invention is that the superabsorbent particles stick to the fibrous substrate, so that the distance between the superabsorbent particles is maintained.

The absorbent composite nonwoven material of the invention is useful in a wide variety of absorbent articles, particularly as an absorbent core material in personal care absorbent articles and medical absorbent articles. Personal care absorbent articles include diapers, training pants, swim wear, absorbent underpants, baby wipes, adult incontinence products, feminine hygiene products and the like. Medical absorbent articles include medical absorbent garments, drapes, gowns, bandages, wound dressings, underpads, wipes, and the like.

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

We claim:

1. A process for making an absorbent composite nonwoven web, comprising the steps of:

providing a first superabsorbent polymer precursor composition;

providing at least one stream carrying a plurality of hydrophilic fibers;

combining the superabsorbent polymer precursor composition with the stream carrying the hydrophilic fibers, to form a mixture;

chemically reacting the superabsorbent polymer precursor composition to form a superabsorbent polymer within the mixture;

depositing the mixture on a forming surface; and forming the absorbent composite nonwoven web from the mixture.

2. The process of claim 1, further comprising the steps of:

providing a primary gas stream which carries the first superabsorbent polymer precursor composition;

providing a secondary gas stream which carries the plurality of hydrophilic fibers; and combining the primary and secondary gas streams to form an integrated stream carrying the mixture.

3. The process of claim 1, further comprising the steps of:

providing at least one primary gas stream carrying a plurality of thermoplastic fibers;

providing a secondary gas stream which carries the plurality of hydrophilic fibers;

providing the first superabsorbent polymer precursor composition in at least one of the primary and secondary gas streams; and combining the primary and secondary streams to form an integrated stream containing the mixture.

4. The process of claim 1, further comprising the steps of:

providing a second superabsorbent polymer precursor composition;

providing a primary gas stream carrying the first superabsorbent polymer precursor composition;

providing a secondary gas stream carrying the plurality of hydrophilic fibers and the second superabsorbent polymer composition;

combining the primary and secondary gas streams to form an integrated stream carrying the mixture; and chemically reacting the first superabsorbent polymer precursor composition with the second superabsorbent polymer precursor composition within the mixture.

5. A process for making an absorbent composite nonwoven web, comprising the steps of:
   forming a first plurality of thermoplastic fibers using a first extrusion apparatus;
   providing a first primary gas stream which carries the first plurality of thermoplastic fibers away form the extrusion apparatus;
   providing a first secondary gas stream carrying a first plurality of absorbent fibers;
   combining the first primary gas stream and the first secondary gas stream to form an integrated stream including a mixture of the thermoplastic fibers and the absorbent fibers;
   providing a first superabsorbent polymer precursor composition;
   chemically reacting the superabsorbent polymer precursor composition to form a superabsorbent polymer within the mixture;
   depositing the mixture onto a forming surface; and
   forming the absorbent composite nonwoven web from the mixture.

6. The process of claim 5, further comprising the steps of:
   forming a second plurality of thermoplastic fibers using a second extrusion apparatus;
   providing a second primary gas stream which carries the second plurality of thermoplastic fibers away from the extrusion apparatus; and
   combining the second primary gas stream with the first primary gas stream and the first secondary gas stream to form the integrated stream including the mixture.

7. The process of claim 5, further comprising the steps of:
   providing a second secondary gas stream carrying a second plurality of absorbent fibers; and
   combining the second secondary gas stream with the first primary gas stream and the first secondary gas stream to form the integrated stream including the mixture.

8. The process of claim 5, further comprising the steps of:
   providing a second superabsorbent polymer precursor composition; and
   chemically reacting the second superabsorbent polymer precursor composition with the first superabsorbent polymer precursor composition within the mixture to form the superabsorbent polymer.

9. The process of claim 5, further comprising the steps of adding the first superabsorbent polymer precursor composition to the first primary gas stream.

10. The process of claim 5, further comprising the step of adding the first superabsorbent polymer precursor composition to the first secondary gas stream.

11. The process of claim 5, further comprising the step of adding the first superabsorbent polymer precursor composition to the integrated stream.

12. The process of claim 5, wherein the thermoplastic fibers comprise meltblown fibers.

13. The process of claim 5, wherein the thermoplastic fibers comprise spunbond fibers.

14. The process of claim 5, wherein the absorbent fibers comprise cellulose fibers.

15. The process of claim 5, wherein the absorbent fibers comprise hydrophilic fibers.

16. The process of claim 5, wherein the absorbent fibers comprise staple fibers.

17. The process of claim 5, wherein the superabsorbent polymer comprises a polymer selected from alkali metal and ammonium salts of poly(acrylic acid) and poly(methacrylic acid), poly(acrylamides), poly(vinylethers), maleic anhydride copolymers with vinyl ethers and alpha-olefins, poly(vinyl pyrrolidone), poly(vinylmorpholinone), poly(vinyl alcohol), and combinations thereof.

18. A process for making an absorbent composite nonwoven web, comprising the steps of:
   providing a first superabsorbent polymer precursor composition including a monomer;
   providing a second superabsorbent polymer precursor composition including a polymerization initiator;
   providing at least one stream carrying a plurality of cellulose fibers;
   combining the first and second superabsorbent polymer precursor compositions with the cellulose fibers to form a mixture;
   chemically reacting the first and second superabsorbent polymer precursor composition to form a superabsorbent polymer;
   depositing the mixture onto the forming surface; and
   forming the absorbent composite nonwoven web from the mixture.

19. The process of claim 18, further comprising the steps of:
   providing at least one stream carrying a plurality of thermoplastic fibers; and
   combining the thermoplastic fibers with the first and second superabsorbent polymer precursor compositions and the cellulose fibers to form the mixture.

20. The process of claim 19, wherein the thermoplastic fibers comprise meltblown fibers.

21. The process of claim 19, wherein the thermoplastic fibers comprise spunbond fibers.

22. The process of claim 18, wherein the polymerization initiator comprises a part of a redox system.

23. The process of claim 18, wherein the monomer comprises a compound selected from the group consisting of aliphatic unsaturated monocarboxylic acids and their salts, methacrylic acids and their salts, unsaturated dicarboxylic acids and their salts, and combinations thereof.

24. The process of claim 18, wherein the monomer comprises a compound selected from the group consisting of acrylic acid and its salts, methacrylic acid and its salts, and combinations thereof.

25. A process for making an absorbent composite nonwoven web, comprising the steps of:
   providing a first superabsorbent polymer precursor composition;
   providing at least one stream carrying a plurality of cellulose fibers;
   combining the superabsorbent polymer precursor composition with the stream carrying the cellulose fibers to form a mixture, while chemically reacting the superabsorbent polymer precursor composition to form a superabsorbent polymer;
   depositing the mixture on a forming surface; and
   forming the absorbent composite nonwoven web from the mixture.

26. The process of claim 25, wherein the chemical reaction commences in an enclosure before the superabsorbent polymer precursor composition is combined with the stream carrying cellulose fibers, and continues thereafter.

* * * * *

UNITED STATES PATENT AND TRADEMARK OFFICE
CERTIFICATE OF CORRECTION

PATENT NO.     : 6,645,407 B2
DATED          : November 11, 2003
INVENTOR(S)    : Kellenberger et al.

It is certified that error appears in the above-identified patent and that said Letters Patent is hereby corrected as shown below:

<u>Drawings,</u>
Fig. 1 should be replaced with the following Fig. 1:

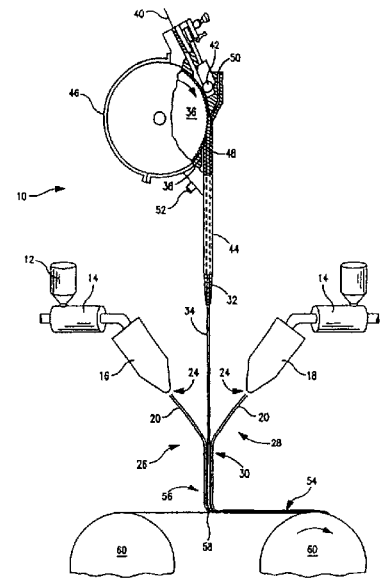

FIG. 1

Fig. 2 should be replaced with the folllowing Fig. 2:

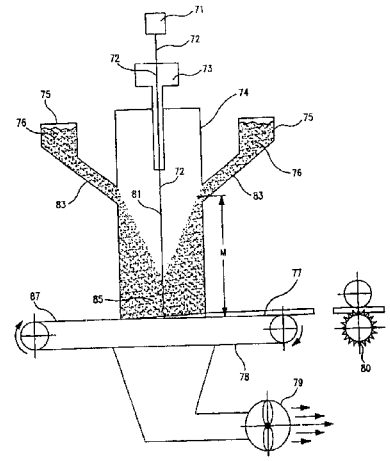

FIG. 2

UNITED STATES PATENT AND TRADEMARK OFFICE
CERTIFICATE OF CORRECTION

PATENT NO. : 6,645,407 B2                              Page 2 of 2
DATED      : November 11, 2003
INVENTOR(S) : Kellenberger et al.

It is certified that error appears in the above-identified patent and that said Letters Patent is hereby corrected as shown below:

Drawings (cont'd),
Fig. 3 should be replaced with the following Fig. 3:

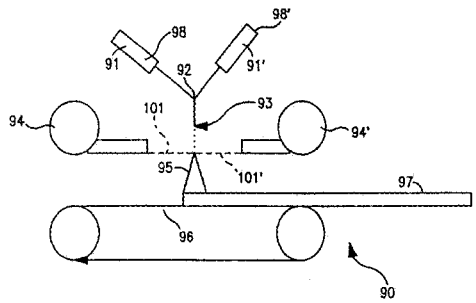

FIG. 3

Fig. 4 should be replaced with the folllowing Fig. 4:

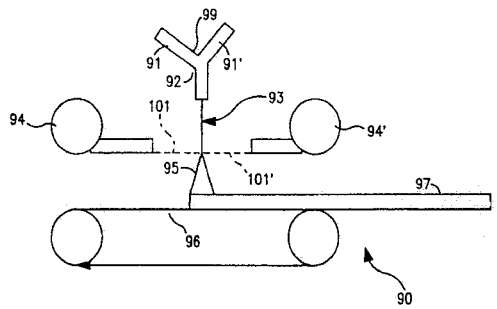

FIG. 4

Signed and Sealed this

Sixteenth Day of March, 2004

JON W. DUDAS
*Acting Director of the United States Patent and Trademark Office*